US007846146B2

(12) United States Patent
Woolston et al.

(10) Patent No.: US 7,846,146 B2
(45) Date of Patent: Dec. 7, 2010

(54) MEDICAMENT CARTRIDGE

(75) Inventors: Robert Woolston, Warwick (GB); Christopher Nigel Langley, Warwickshire (GB); Lee Simon Adams, Warwick (GB)

(73) Assignee: DCA Design International Limited, Warwick (GB)

( * ) Notice: Subject to any disclaimer, the term of this patent is extended or adjusted under 35 U.S.C. 154(b) by 95 days.

(21) Appl. No.: 12/076,333

(22) Filed: Mar. 17, 2008

(65) Prior Publication Data

US 2008/0228148 A1 Sep. 18, 2008

Related U.S. Application Data

(63) Continuation of application No. 10/307,300, filed on Dec. 2, 2002, now Pat. No. 7,637,899.

(30) Foreign Application Priority Data

Dec. 6, 2001 (GB) ................................. 0129171.5

(51) Int. Cl.
*A61B 19/00* (2006.01)

(52) U.S. Cl. ..................................... 604/415

(58) Field of Classification Search ......... 604/195–236, 604/411–415
See application file for complete search history.

(56) References Cited

U.S. PATENT DOCUMENTS

| 3,150,661 A | 9/1964 | Maki |
| 3,974,832 A | 8/1976 | Kruck |
| 4,153,056 A * | 5/1979 | Silver et al. .................. 604/211 |
| 5,135,514 A | 8/1992 | Kimber |
| 5,226,901 A | 7/1993 | Dhaliwal et al. |
| 5,334,162 A * | 8/1994 | Harris ......................... 604/232 |
| 5,389,086 A | 2/1995 | Attermeier et al. |
| 5,454,786 A | 10/1995 | Harris |
| 5,554,134 A | 9/1996 | Bonnichsen |
| 5,709,666 A | 1/1998 | Reynolds |
| 5,989,227 A | 11/1999 | Vetter et al. |
| 6,004,297 A | 12/1999 | Steenfeldt-Jensen et al. |
| 6,126,646 A | 10/2000 | Hansen et al. |

FOREIGN PATENT DOCUMENTS

| CZ | 286 666 | 2/2000 |
| GB | 1 602 090 | 11/1981 |
| HU | 210 361 B | 2/1989 |
| HU | 222 513 B1 | 1/1999 |
| WO | WO 97 14461 | 4/1997 |
| WO | WO 99 16485 | 4/1999 |
| WO | WO 03/047667 A1 | 6/2003 |

* cited by examiner

*Primary Examiner*—Leslie R Deak
(74) *Attorney, Agent, or Firm*—Oliff & Berridge, PLC

(57) ABSTRACT

Many of those having diabetes take a combination of slow and fast acting types of insulin. It is important that the different forms of medicament do not become confused. To this end, a medicament cartridge is provided comprising a sleeve having a bottleneck providing a flange at a first end, a fluid impermeable membrane secured across the first end by a metal cap beaded beneath the flange, and a displaceable piston located internally of the sleeve towards a second end of the sleeve, a collar located against an external periphery of the cartridge housing beneath the flange and an adaptor top press fit over the cap and the collar, the adaptor top being provided with means to act upon the collar thereby to retain the adaptor top on the sleeve.

8 Claims, 2 Drawing Sheets

MEDICAMENT CARTRIDGE

This is a Continuation of application Ser. No. 10/307,300 filed Dec. 2, 2002. The disclosure of the prior application is hereby incorporated by reference herein in its entirety.

FIELD OF THE INVENTION

The present invention relates to improvements in and relating to medicament cartridges for use with medication delivery apparatus, and in particular but not exclusively to medicament cartridges for injector pens and infusers.

BACKGROUND TO THE INVENTION

It is known that a person providing themselves, or others, with a medicament regimen may require more than one medicament as part of that regimen. For example many of those having diabetes take a combination of slow and fast acting types of insulin. It is important that the different forms of medicament do not become confused and that the patient does not receive the incorrect medicament. It is thus advantageous that different forms of medicament are provided in medicament cartridges that can readily be distinguished.

However, in the manufacture of medicament cartridges, it is desirable, in order that advantage may be taken of economies of scale that as few different manufacturing steps as possible exist as between medicament cartridges containing different medicaments.

A number of solutions to this problem are already known. For example, in U.S. Pat. No. 6,126,646 an adaptor top for fitting to a medicament cartridge is disclosed. The adaptor top has a depending skirt, the skirt being provided with an internally directed, circumferentially extending bead. The bead in use is seated beneath and against a metal cap of the medicament cartridge. In order to be placed over the cap the skirt is made very flexible or provided with a number of longitudinally extending slits. To prevent the skirt from being removed, a ring is placed over the skirt to prevent the beaded portion of the skirt from coming loose. However, should the ring in use become loose or inadvertently be dislodged, the adaptor top may easily or inadvertently become separated from the medicament cartridge.

The present invention provides a further solution to the problem of balancing the requirements presented above.

SUMMARY OF THE INVENTION

According to the present invention a medicament cartridge comprises a sleeve having a bottleneck providing a flange at a first end, a fluid impermeable membrane secured across the first end by a metal cap beaded beneath the flange, and a displaceable piston located internally of the sleeve towards a second end of the sleeve, a collar located against an external periphery of the cartridge housing beneath the flange and an adaptor top press fit over the cap and the collar, the adaptor top being provided with means to act upon the collar thereby to retain the adaptor top on the sleeve.

Since the collar is retained within the adaptor top there is no risk that it may work loose.

Preferably, the collar is adhered to the cartridge housing.

Preferably, the collar is defined by a first inner surface that conforms to a peripheral surface of the sleeve and a second outer surface. More preferably, the second outer surface provides a smooth rounded surface.

Preferably, the collar is formed as a hinged member.

Preferably the collar has a first end provided with a male coupling and a second end provided with a female coupling to received the male coupling.

BRIEF DESCRIPTION OF THE DRAWINGS

The invention will now be described, by way of example only, with reference to the accompanying drawings in which:

FIG. 1 shows an exploded view of a medicament cartridge in accordance with the invention; and.

DETAILED DESCRIPTION OF THE INVENTION

Figure 1:
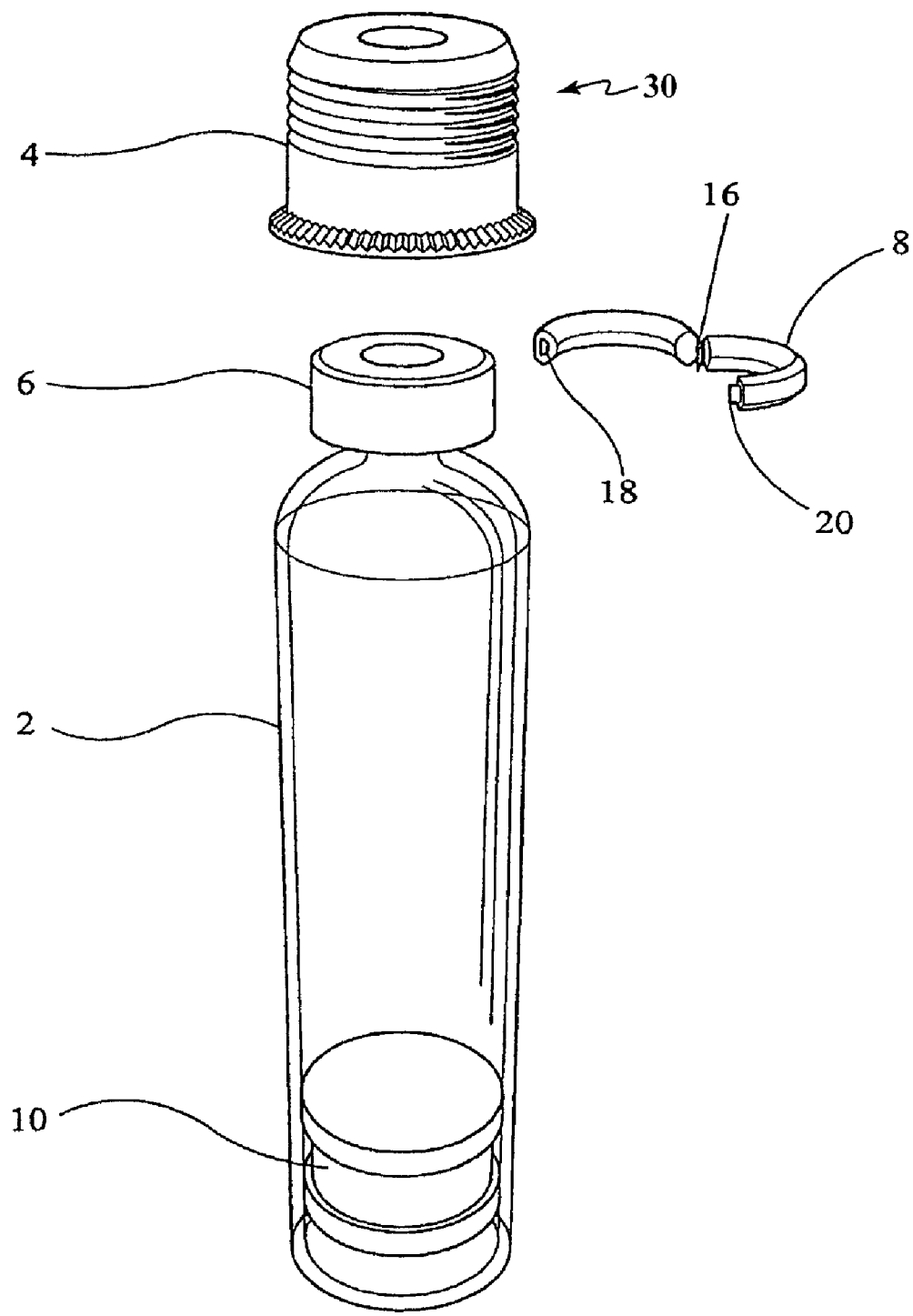
Figure 2:
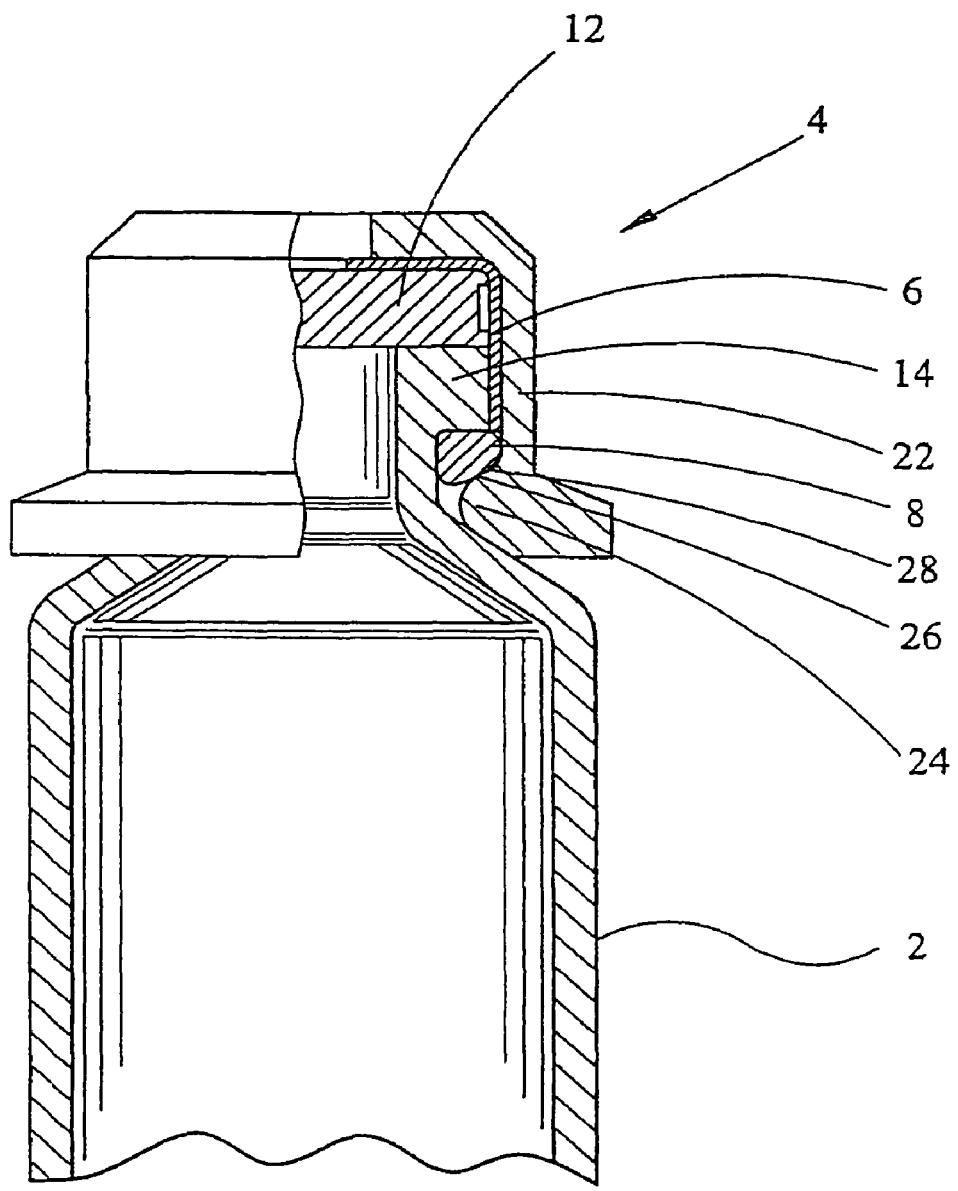
FIG. 2 shows a side section through an assembled medicament cartridge in accordance with the present invention.

Referring to FIG. 1 and FIG. 2, there may be seen a medicament cartridge in accordance with an exemplary embodiment of the present invention.

The medicament cartridge comprises a cylinder, sleeve or cartridge housing 2 of a clear material such as a glass. A first end of the sleeve 2 is closed by a moveable piston 10. A second end of the sleeve 2 is formed as a bottleneck having a flange 14, and is closed by a fluid impermeable membrane 12. A metal cap 6 extends over an upper surface of the membrane 12 and is beaded beneath the flange 14 to secure the membrane in position. An upper portion of the cap is provided with an aperture through which, in use, the membrane 12 may be pierced by a needle arrangement.

A collar 8 is also shown. In the illustrated embodiment the collar 8 is of hinged form. A hinge 16 separates a first end of the collar having a female coupling 18 from a second end of the collar 8 having a male coupling 20. In use, the male coupling 20 is received by the female coupling 18. The female coupling 18 and the male coupling 20 may be conveniently press fit or snap fit together.

An adaptor top 4 may then be pressed down over the metal cap 6 and the associated collar 8. The adaptor top 4 has peripheral skirt 22 provided with a radially directed internal flange or bead 24. The skirt 22 and the bead 24 are so disposed that when the adaptor top 4 is pressed down fully over the cap 6 and collar 8 an upper surface 26 of the bead 24 is in abutment with a lower surface 28 of the collar 8. This has the effect of retaining the adaptor top 4 in position.

The adaptor top 4 is formed from any suitable material. The adaptor top 4 should be made of a material sufficiently flexible that the peripheral skirt 22 can elastically deform about the metal cap 6, the collar 8 and the flange 14.

It will be understood that by manufacturing the adaptor top 4 of plastics material, the material may be colour coded to provide an indication of the nature of the medicament contained within the medicament cartridge.

The adaptor top 4 may conveniently be provided with a screw thread 30 or other means by which a needle unit may be secured to the medicament cartridge.

In order to dispense medicament from within the medicament cartridge, the piston 10 is urged towards the second end of the sleeve 2 to dispense medicament through a needle forming a part of the needle arrangement.

What is claimed is:

1. A medicament cartridge comprising:
   a sleeve having a first end and a second end;
   a bottleneck disposed at the second end;
   a flange disposed at the bottleneck;
   a cap;
   a fluid impermeable membrane secured across the second end by the cap, the cap being beaded beneath the flange;

a displaceable piston located internally of the sleeve towards the first end of the sleeve;

a collar located against an external periphery of the sleeve beneath the flange and having a lower surface; and an adaptor top in a press fit over the cap and the collar, the adaptor top having means that act upon the collar to retain the adaptor top on the sleeve, the means being directed radially inwardly of the adaptor top to abut with the lower surface of the collar.

2. A medicament cartridge according to claim 1, wherein the collar is adhered to the sleeve.

3. A medicament cartridge according to claim 1, wherein the collar is defined by a first inner surface that conforms to a peripheral surface of the sleeve and a second outer surface.

4. A medicament cartridge according to claim 3, wherein the second outer surface provides a smooth rounded surface.

5. A medicament cartridge according to claim 1, wherein the collar is formed as a hinged member.

6. A medicament cartridge according to claim 1, wherein the collar has a first end provided with a male coupling and a second end provided with a female coupling to receive the male coupling.

7. A medicament cartridge according to claim 1, wherein the cap is a metal cap.

8. A medicament cartridge according to claim 1, the adapter top comprising means by which a needle unit may be secured to the medicament cartridge.

* * * * *